(12) United States Patent
Han et al.

(10) Patent No.: US 8,618,145 B2
(45) Date of Patent: Dec. 31, 2013

(54) SMALL MOLECULAR COMPOUNDS CAPABLE OF ACCELERATING PROLIFERATION OF STEM CELLS AND USE THEREOF

(76) Inventors: Mei Han, Beijing (CN); Yan Feng, Beijing (CN); Yuanyuan Sun, Beijing (CN)

( * ) Notice: Subject to any disclaimer, the term of this patent is extended or adjusted under 35 U.S.C. 154(b) by 13 days.

(21) Appl. No.: 13/320,203

(22) PCT Filed: May 12, 2009

(86) PCT No.: PCT/CN2009/000512
§ 371 (c)(1),
(2), (4) Date: Nov. 11, 2011

(87) PCT Pub. No.: WO2010/130063
PCT Pub. Date: Nov. 18, 2010

(65) Prior Publication Data
US 2012/0053214 A1    Mar. 1, 2012

(51) Int. Cl.
*A61K 31/4245*    (2006.01)
*C07D 271/113*    (2006.01)

(52) U.S. Cl.
USPC .......................................... 514/364; 548/144

(58) Field of Classification Search
USPC .......................................... 514/364; 548/144
See application file for complete search history.

(56) References Cited

FOREIGN PATENT DOCUMENTS

| CN | 101519385 | | 9/2009 |
|---|---|---|---|
| JP | 07084349 A | * | 3/1995 |
| WO | 9745111 | | 12/1997 |
| WO | 03093250 | | 11/2003 |
| WO | 2005092843 | | 10/2005 |

OTHER PUBLICATIONS

Rollas et al. Archiv der Pharmazie (1991), vol. 324(3), p. 189-190.*
Compound (CAS RN 1024522-98-2) (2008).*
International Search Report for PCT/CN2009/000512 dated Feb. 11, 2010.

* cited by examiner

*Primary Examiner* — Yong Chu
(74) *Attorney, Agent, or Firm* — RatnerPrestia

(57) ABSTRACT

The invention provides small molecule compounds capable of accelerating proliferation of stem cells and uses thereof. The compounds play an important role in the research of stem cell proliferation mechanism. The invention further relates to the uses of the compounds and relevant compounds thereof in the preparation of stem cell proliferation accelerators and the preparation of medicines accelerating stem cell proliferation. The invention also relates to the uses of the compounds in the preparation of medicines for the treatment of various diseases arising from functional cells loss or damage. The diseases arising from stem cell trauma comprise diseases related to the degeneration or damage of nervous system cells, blood system diseases, diseases related to the loss or damage of cardiovascular cells, skin burn and the like.

4 Claims, 7 Drawing Sheets

AD1-3

Administration (2)3-3

SMALL MOLECULAR COMPOUNDS CAPABLE OF ACCELERATING PROLIFERATION OF STEM CELLS AND USE THEREOF

CROSS-REFERENCE TO RELATED APPLICATION

This application is a U.S. National Phase Application of PCT International Application PCT/CN2009/000512, filed May 12, 2009, the contents of which are incorporated herein by reference in their entireties for all purposes.

FIELD OF THE INVENTION

The invention relates to small molecular compounds capable of accelerating proliferation of stem cells, and further relates to the uses of the small molecular compound in the preparation of stem cell proliferation accelerators and in the preparation of medicines accelerating stem cell proliferation. The invention also relates to the use of the small molecular compounds in the preparation of medicines for treating the diseases related to the loss or damage of cells. Furthermore, the invention further relates to a method of administrating the small molecular compound according to the invention to the patients in need thereof so as to treat these diseases. The invention belongs to the field of medicines.

BACKGROUND OF THE INVENTION

Stem cells are initial cells characterized by their ability to renew themselves and their potency to be differentiated into a diverse range of specialized functional cell type. Under specific conditions, stem cells can also be proliferated and differentiated into different functional cells. Therefore, studies on stem cells play an important role in renewment and traumatism repairment of tissues and organs in organisms, and may become the only hope for many incurable diseases, especially diseases related to loss or damage of cells and tissues. Stem cells include embryonic stem cells and adult stem cells. Application of embryonic stem cells is greatly restricted due to ethical issues. Since adult stem cells can be differentiated into functional cells and tissues, they provide the basis for wide application of stem cells, provide a good model in vitro for studies on early development of mammals, provide new sources for cell replacement therapies of many diseases, and also represent that development of modern biology and development of new drugs enter a new era. Thus, adult stem cells become the focus of scientific studies. However, normal adult mammalian stem cells are very few and are in resting state, and they are very hard to differentiate into one specific cell type since the differentiation and development thereof depend on multiple factors such as inner regulation mechanisms and micro-environments. It is hard to large-scale culture them in vitro for a long term, especially to culture and amplify them under serum free conditions. Thus, they cannot be applied to actual treatments. So far, only a few adult tissue stem cells can be cultured and amplify in vitro under serum free conditions, but, different growth factors, signaling molecules and the like need to be added to perform genetic regulation. Obviously, more effective and more selective cell culture materials and induction techniques are required in autologous and in vitro directed induction of proliferation and differentiation of stem cells so as to generate specific type of homologous cell population.

Many diseases can trace back to lost or damaged functional cells, and cell replacement therapy is an effective and sometimes, even the only method for treatment of these diseases. Cell replacement therapy is classified into cell transplantation and regulation of proliferation and directed differentiation of autologous stem cells by medicines. Stem cell drugs is a class of therapeutic and preventive medicines capable of preventing and treating diseases caused by loss or damage of cells by regulating stem cell proliferation and differentiations in organisms. It is found in recent years that both growth factors and small molecular compounds can regulate the proliferation and differentiation of stem cells in organisms. Application of stem cell drugs to regulate proliferation and potency of directed differentiation of autologous stem cells so as to rebuild the damaged functional cells and recover their biological function, not only solves the difficulty on the source of adult stem cell, but also avoids the ethical issues of embryonic stem cells as well as these problems involving cell transplantation immune rejection and post-surgical complications, and provides a completely new viewpoint and strategy for the treatment and prevention of diseases related to the lost or damaged functional cells.

For example, central nervous system diseases—neural degenerative or damaged disease, including Parkinson's disease (PD), Alzheimer's disease (AD), Huntington's disease (HD), drug abuse, depression, cerebral apoplexy and the like, all of which are caused by loss and damage of neural cells. An ideal treatment strategy is to save damaged neural cells as much as possible and at the same time to stimulate regeneration of the neural cells. Currently, the damaged cells are tried to be repaired by transplantation of neural stem cells. However, there is a limitation on the obtainment of neural stem cells and functional cells for transplantation in clinic, as well as problems such as the ones involving cell transplantation immune rejection and post-surgical complications. Therefore, people have to focus on stimulation of proliferation and differentiation of autologous neural stem cells so as to provide the possibility of renewing the neural stem cells, and further to promote the development of neural stem cell drugs.

Growth factors or biologically active proteins can be used as stem cell drugs. However, growth factors or biologically active proteins as active micromolecule not only interferes with complicated physiological process to exhibit complicated multiple regulation functions, but also initiate immune response as heterologous peptides or proteins. Moreover, they are expensive and hardly have clinical treatment and medicinal use. Small molecular compounds are primary drugs in clinic for the treatment of diseases all the time, and people pay more and more attention to them because of their potential as stem cell regulation medicines.

Small molecular compounds include synthetic small molecular compounds and natural small molecular compounds (which mainly refer to compounds extracted from plants and active components of herbs). By comparison, small molecular medicines have the following characteristics and advantages.

a. For regulation resulted from small molecular compounds, the small molecular compounds are not only easy to be administrated, but also easy to be removed after recover of the physiological function, which is convenient for regulation of pathogenic and physiological process.

b. Unlike endogenous macromolecular active substances, which interfere with complicated multiple control systems in vivo and are easy to initiate immune response, exogenous small molecular compounds generally have a single regulation effect, and therefore are helpful for the retainment of normal physiological functions in organisms.

c. Small molecular compounds are easy to be artificially synthesized, and have a better medicinal value and clinic value in treatment than endogenous active macromolecular.

d. Especially natural small molecular compounds have a better biological adaptability, particularly lower toxicity as compared to the synthetic small molecular compounds as they have underwent biological (plant) metabolism.

e. Small molecular compounds are easy to cross blood brain barrier due to their small molecular weight.

Therefore, it is not only a hotspot in biological studies on in vitro proliferation and differentiation of adult stem cells but also a hotspot in studies on inventive drugs development—stem cell drugs to search small molecular compounds capable of specifically regulating adult stem cells proliferation and differentiation.

The purpose of the invention is to provide the small molecular compounds capable of accelerating proliferation of stem cells. The small molecular compounds can be used as stem cell proliferation accelerators and be used to prepare medicines accelerating stem cell proliferation, and provides more options for scientific research, clinic and medicines. Application of stem cell drugs to regulation of the proliferation and the potency of specific differentiation of autologous stem cells so as to rebuild the damaged functional cells and recover their biological functions, not only solves the difficulty relating to the source of adult stem cells, but also avoids the ethical restrictions of embryonic stem cells as well as the problem involving cell transplantation immune rejection and post-surgical complications, which provides new prospect and strategy for preventing and treatment of diseases related to the lost or damaged cells.

SUMMARY OF THE INVENTION

The purpose of the invention is to provide a small molecular compound capable of accelerating proliferation of stem cells. The small molecular compounds provided in the invention can be used as stem cell proliferation accelerators and be used to prepare medicines accelerating stem cell proliferation, and can provide a large number of stem cells for transplantation when being applied in clinic. The small molecular compounds provided in the invention can accelerate stem cell proliferation and functional cell repairment, and can be used in studies on stem cell proliferation mechanism.

Compounds and Methods for the Preparation of the Same

The invention provides a compound of formula (I), or pharmaceutically acceptable salts, isomers or hydrates thereof:

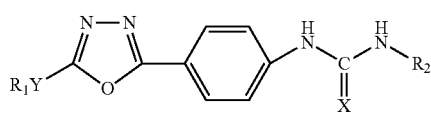

[I]

Wherein, $R_1$ is hydrogen, lower alkyl, or aryl; $R_2$ is amino, substituted amino, lower alkyl or aryl; X is heteroatom, such as oxygen, or sulfur; Y is heteroatom, such as oxygen, or sulfur.

In the invention, lower alkyl refers to C1-C6 alkyl (alkyl with 1-6 carbons), includes C1-C4 alkyl, such as methyl, ethyl, propyl, or butyl. Aryl comprises, but is not limited to phenyl or naphthyl. Heteroatom generally refers to O, S, or N atom, preferably oxygen or sulfur.

The preferred examples of the above formula are as follows.

In a preferred embodiment, the small molecular compound of formula (I) is Ia ($R_1$ is hydrogen, $R_2$ is amino, X is sulfur, Y is sulfur), the structural formula is as follows:

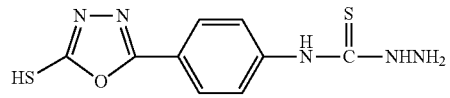

In a preferred embodiment, the small molecular compound of formula (I) is Ib ($R_1$ is methyl, $R_2$ is amino, X is sulfur, Y is sulfur), the structural formula is as follows:

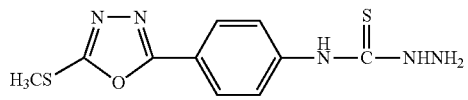

In a preferred embodiment, the small molecular compound of formula (I) is Ic ($R_1$ is methyl, $R_2$ is methyl, X is sulfur, Y is sulfur), the structural formula is as follows:

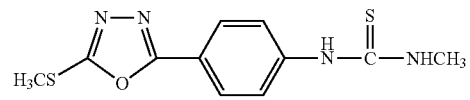

In a preferred embodiment, the small molecular compound of formula (I) is Id ($R_1$ is hydrogen, $R_2$ is amino, X is oxygen, Y is sulfur), the structural formula is as follows:

In a preferred embodiment, the small molecular compound of formula (I) is Ie ($R_1$ is hydrogen, $R_2$ is substituted amino, X is sulfur, Y is sulfur), the structural formula is as follows:

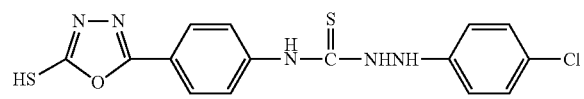

In a preferred embodiment, the small molecular compound of formula (I) is If ($R_1$ is hydrogen, $R_2$ is substituted amino, X is sulfur, Y is sulfur), the structural formula is as follows:

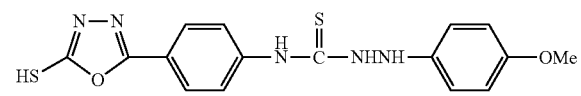

In a preferred embodiment, the small molecular compound of formula (I) is Ig ($R_1$ is hydrogen, $R_2$ is methyl, X is sulfur, Y is oxygen), the structural formula is as follows:

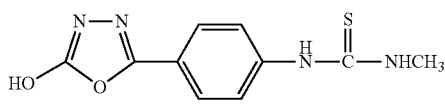

The invention also relates to a method for preparing the small molecular compound of formula (I):

Scheme 1:

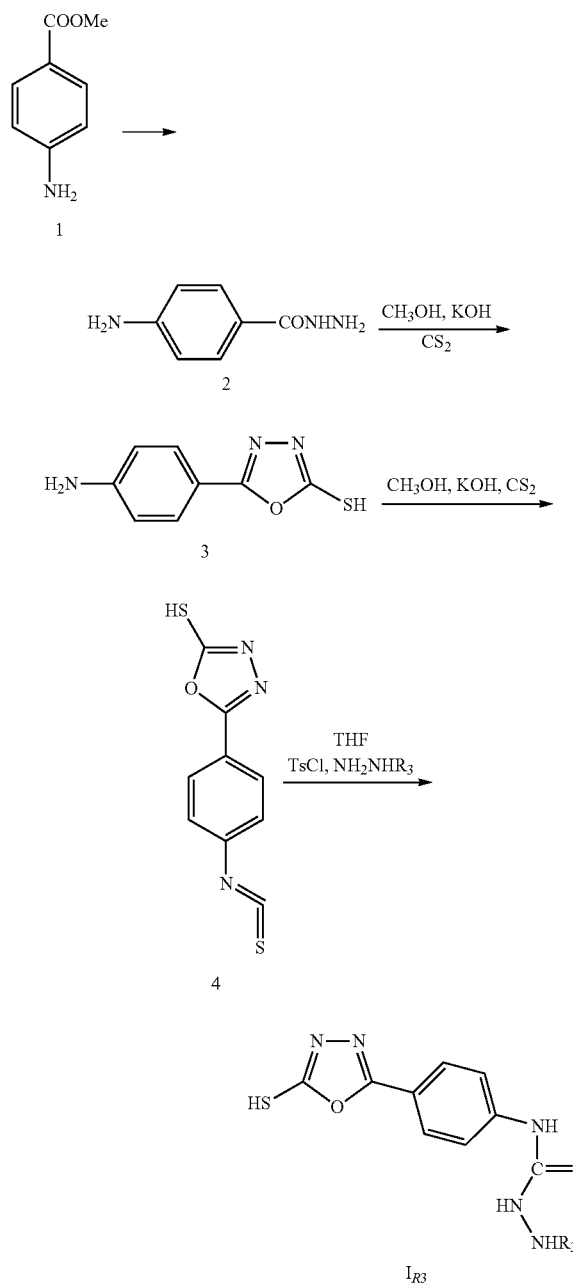

Scheme 1 refers to a process, wherein compound 1 as the raw material is cyclized into the intermediate product 3, and then thiosemicarbazone reaction is performed to prepare $I_{R3}$ ($R_3$ is hydrogen, substituted aryl).

Scheme 2:

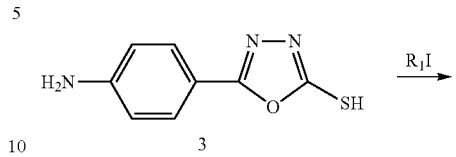

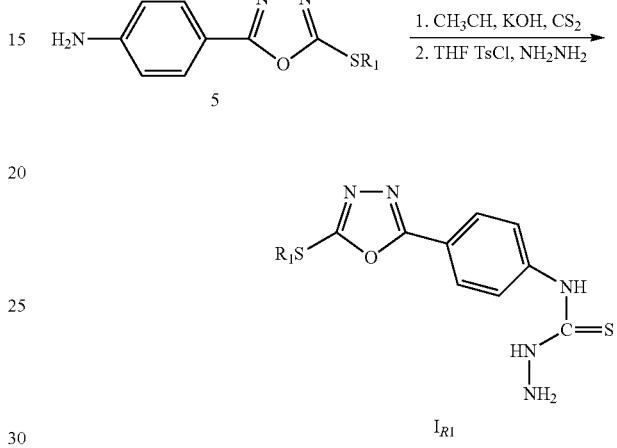

(in the formula: $R_1$ is lower alkyl, aryl)

Scheme 2 refers to a process, wherein the compound 3 in Scheme 1 as the raw material is subjected to alkylization first, and then is subjected to thiosemicarbazone reaction to prepare a compound of formula $I_{R1}$ ($R_1$ is lower alkyl, aryl).

Scheme 3:

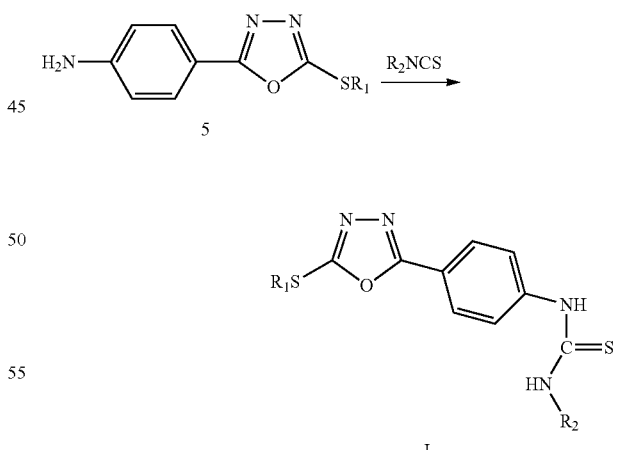

(in the formula, $R_1$ is lower alkyl, aryl; $R_2$ is lower alkyl, aryl)

Scheme 3 refers to a process, wherein the compound 5 in Scheme 2 as the raw material is reacted with the compound $R_2NCS$ to prepare a compound of formula $I_{R1R2}$ ($R_1$ is lower alkyl, aryl; $R_2$ is lower alkyl, aryl).

Scheme 4:

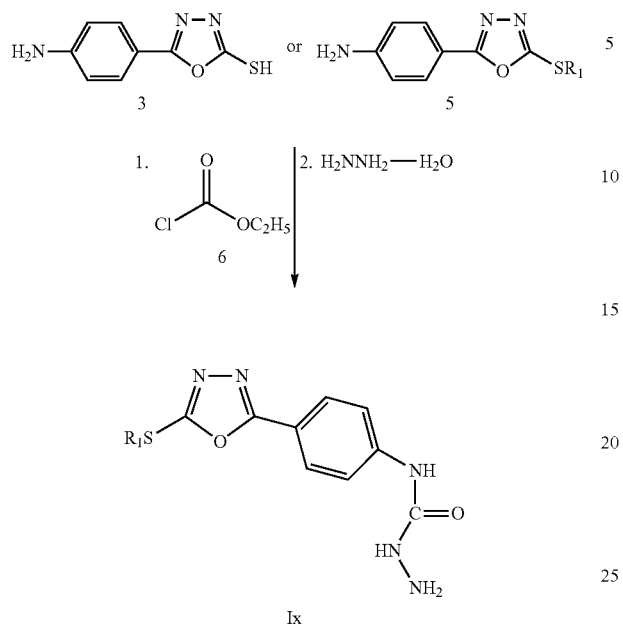

(in the formula, $R_1$ is hydrogen, lower alkyl, aryl)

Scheme 4 refers to a process, wherein the compound 3 in Scheme 1 or the compound 5 in Scheme 2 as the raw material is reacted with the compound 6 to prepare a compound of formula Ix ($R_1$ is hydrogen, lower alkyl, aryl).

Scheme 5:

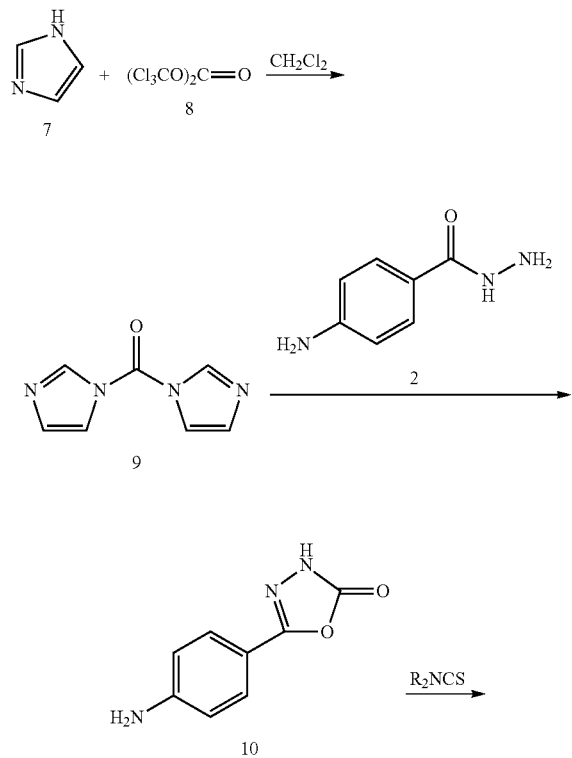

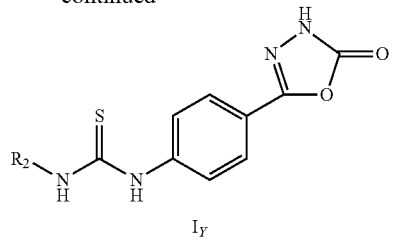

Scheme 5 refers to a process, wherein the compound 7 and compound 8 are used as the raw materials to synthesize the intermediate product 9, which is then reacted with the compound 2 to produce the compound 10, and a reaction similar to Scheme 3 is performed to prepare a compound of $I_Y$ ($R_2$ is amino, substituted amino, lower alkyl, aryl).

The compounds of formula (I) obtained in Schemes 1-5 can be separated by conventional methods. Conventional separation methods, such as recrystallization, thin layer chromatography for separation, column chromatography, and the like, can be used in purification as required. In addition, the compounds can be purified in a form of salt as required.

Compound (I) can be converted into pharmaceutically acceptable salts by well-known methods.

Proliferation Agent

The invention also relates to the use of the small molecular compound of formula (I) provided in the invention in the preparation of a stem cell proliferation accelerator. Said stem cell proliferation accelerator refers to a compound and components thereof capable of accelerating stem cell proliferation when being contacted with stem cells in vivo or in vitro.

The invention also relates to the compound of formula (I) as stem cell proliferation accelerator.

The invention also relates to the use of the compound of formula (I) as stem cell proliferation accelerator.

Due to the foregoing functions and characteristics of the compounds according to the invention, the compounds according to the invention can be used as additives during in vitro culturing of stem cells. Unlike the macromolecular proteins used in the prior art, the compounds according to the invention are small molecular substances with a small molecular weight, and can retain the properties in medium for a long term (the medium is replaced once every about 7 to 9 days). Furthermore, after reading the description of the invention, a person skilled in the art can envisage that the compounds according to the invention can be used as additives for culturing stem cells so as to accelerate their proliferation, which is a better and new experimental additive of serum free cell culture for the studies on stem cells.

In said uses, the stem cell proliferation accelerator uses the small molecular compound of formula (I) provided in the invention as the active component. The stem cell proliferation accelerator provided in the invention can use the small molecular compound provided in the invention alone, or is a mixture of the small molecular compound provided in the invention with any other effective component having an effect of accelerating stem cell proliferation.

The stem cell proliferation accelerator according to the invention can be used in a method for proliferation of stem cells, characterized by contacting the small molecular compound with stem cells so as to accelerate stem cell proliferation. Under the occasions where the stem cell proliferation accelerator is used in vitro, the small molecular compound provided in the invention is preferably dissolved in the substances that can dissolve it before using it. The solvents can be exemplified as water, DMSO and the like.

No specific restriction is made to stem cells as long as they are stem cells, including adult stem cells and embryonic stem cells. Embryonic stem cells as totipotent cells can be differentiated into any cell types; adult stem cells include neural stem cells, mesenchymal stem cells, hematopoietic stem cells and the like.

The stem cell proliferation accelerators prepared from the small molecular compounds of formula (I) provided in the invention can be directly administrated. However, it is intended to provide them as conventional medicines, which can be applied to animals or humans.

No specific restriction is made to stem cells as long as they are stem cells, including adult stem cells and embryonic stem cells. Adult stem cells include neural stem cells, mesenchymal stem cells, hematopoietic stem cells and the like. Embryonic stem cells as totipotent cells can be differentiated into any cell types.

In said uses, the stem cell proliferation accelerator uses the small molecular compound of formula (I) provided in the invention as the active component. The stem cell proliferation accelerator provided in the invention can comprise the small molecular compound provided in the invention alone, or is a mixture of the small molecular compound provided in the invention and any other effective component having an effect of accelerating stem cell proliferation. These medicines can be prepared according to the methods for preparing the formulation of the stem cell proliferation accelerator, and can also be administrated in the same manner.

The stem cell proliferation accelerator according to the invention can be used in a method for proliferation of stem cells, characterized by contacting the small molecular compound with stem cells so as to accelerate stem cell proliferation. Under the occasions where the stem cell proliferation accelerator is used in vitro, the small molecular compound provided in the invention is preferably dissolved in the substances that can dissolve it before using it. The solvents can be exemplified as water, DMSO and the like.

Methods

The invention also relates to a method for accelerating proliferation of stem cells, characterized in that the small molecular compound of formula (I) provided in the invention is used to accelerate the proliferation of stem cells.

The invention also relates to a method for accelerating proliferation of stem cells, characterized in that the small molecular compound of formula (I) provided in the invention is contacted with stem cells.

The above methods according to the invention can be performed in vivo or in vitro.

The invention also relates to a method for treating diseases by administrating the small molecular compound of formula (I) to patient in need thereof.

In the method, the patient in need thereof may be a patient suffering from the following diseases: diseases related to the loss or traumatism of cells selected from the group consisting of diseases related to the neural degeneration or damage, blood system diseases, diseases related to the loss or damage of cardiovascular cells, and skin diseases.

In particular, the patient in need thereof may be a patient suffering from the following diseases: said diseases related to the neural degeneration or damage, selected from the group consisting of Parkinson's disease, Alzheimer's disease, Huntington's disease, Down's syndrome, Cerebrovascular disorders, Stroke, spinal cord injury, multiple sclerosis, amyotrophic lateral sclerosis, epilepsy, anxiety disorder, depression, and bipolar disorder; blood system diseases, selected from the group consisting of aplastic anemia, thalassemia, leukemia, and hematopoietic and immune system disorders caused after radiotherapy and chemotherapy for malignant neoplasm; diseases related to the loss or damage of cardiovascular cells, selected from the group consisting of myocardiosis, coronary heart disease, heart failure, subacute endocarditis, acute myocardial infarction, angina pectoris, and ischemic heart disease; skin disease is skin burn.

The invention further provides a method for culturing stem cells, comprising culturing stem cells in the presence of the compound according to the invention.

In an embodiment, stem cells are obtained in the presence of the stem cell proliferation accelerator according to the invention.

The proliferation of stem cells can be effectively accelerated by culturing animal stem cells in the presence of the stem cell proliferation accelerator according to the invention. Animal stem cells may be stem cells from any animal, preferably stem cells from mammalian, more preferably from rat, mouse, monkey, and human. Stem cells may be exemplified as neural stem cells, hematopoietic stem cells, mesenchymal stem cells and the like from brain, preferably neural stem cells. Neural stem cells may be cells from animal at any week or year age, but preferably adult stem cells. The stem cells according to the invention may include human embryonic stem cells, or in another embodiment, the stem cells according to the invention include human embryonic stem cells.

Methods for obtaining adult neural stem cells from animals may be exemplified as the methods wherein tissue cells from rat SVZ region are obtained and isolated so as to culture rat neural stem cells.

When culturing neural stem cells in the presence of the stem cell proliferation accelerator according to the invention, preferably the concentration of the neural stem cell proliferation accelerator is between 1 nmol/ml and 100 µmol/ml per about $2 \times 10^4$ cells/ml. The proliferation of neural stem cells can be accelerated by contacting the neural stem cells with the stem cell proliferation accelerator according to the invention, culturing them at 37° C. in 5% $CO_2$ atmosphere, and replacing the whole medium or a part of the medium once every three days during 2~7 days.

The medium for culturing adult neural stem cells can be any medium as long as it does not disturb acceleration of neural stem cell proliferation, and DMEM/F12 medium is preferably used.

The neural stem cells can be obtained from the medium according to the culturing methods, and be transplanted to the damaged positions of the patients suffering from nervous diseases, that is, can be used to treat the nervous system diseases. The diseases may be exemplified as Parkinson's disease, Alzheimer's disease, Down's syndrome, Cerebrovascular disorders, Stroke, spinal cord injury, Huntington's disease, multiple sclerosis, amyotrophic lateral sclerosis, epilepsy, anxiety disorder, comprehensive disorder, depression, bipolar disorder and the like.

Composition and Medicinal Use Thereof

It is known that small molecular compounds are easy to cross blood brain barrier to reach brain cells. Currently, the United States Food and Drug Administration (FDA) actively are processing the treatment mode of human stem cell transplantation. The small molecular compounds among the compounds according to the invention accelerate the survival of stem cells under conditions of serum free and low cell density. Due to the characteristics of the compounds according to the invention, after reading the foregoing description, a person skilled in the art can understand that the compounds according to the invention can be further developed into a medicinal compound by known techniques.

The another purpose of the invention is to provide a pharmaceutical composition, comprising the small molecular compounds of formula (I) or pharmaceutically acceptable salts, isomers, or hydrates thereof.

The pharmaceutical composition provided in the invention may comprise a therapeutically effective amount of the small molecular compound of formula (I) or pharmaceutically acceptable salts, isomers, or hydrates thereof only. Alternatively, the pharmaceutical composition provided in the invention may also comprise a therapeutically effective amount of the small molecular compound of formula (I) or pharmaceutically acceptable salts, isomers, or hydrates thereof, and pharmaceutically acceptable carriers or excipients. Alternatively, the pharmaceutical composition provided in the invention may comprises a therapeutically effective amount of the small molecular compound of formula (I) or pharmaceutically acceptable salts, isomers, or hydrates thereof, additional active components for treatment and pharmaceutically acceptable carriers or excipients.

The pharmaceutical composition provided in the invention may comprise a therapeutically effective amount of the small molecular compound of formula (I) and pharmaceutically acceptable carriers or excipients.

The pharmaceutical composition provided in the invention may comprise a therapeutically effective amount of small molecular compound Ia and pharmaceutically acceptable carriers or excipients.

The pharmaceutical composition provided in the invention may comprise a therapeutically effective amount of small molecular compound Ib and pharmaceutically acceptable carriers or excipients.

The pharmaceutical composition provided in the invention may comprise a therapeutically effective amount of small molecular compound Ic and pharmaceutically acceptable carriers or excipients.

The pharmaceutical composition provided in the invention may comprise a therapeutically effective amount of small molecular compound Id and pharmaceutically acceptable carriers or excipients.

The pharmaceutical composition provided in the invention may comprise a therapeutically effective amount of small molecular compound Ie and pharmaceutically acceptable carriers or excipients.

The pharmaceutical composition provided in the invention may comprise a therapeutically effective amount of small molecular compound If and pharmaceutically acceptable carriers or excipients.

The pharmaceutical composition provided in the invention may comprise a therapeutically effective amount of small molecular compound Ig and pharmaceutically acceptable carriers or excipients.

The pharmaceutical composition provided in the invention may comprise a therapeutically effective amount of the combination of one or more of the small molecular compounds Ia, Ib, Ic, Id, Ie, If, and Ig, and pharmaceutically acceptable carriers or excipients.

The pharmaceutical composition provided in the invention comprises any acceptable forms, which can be prepared by mixing the active component with one or more pharmaceutically acceptable carriers in accordance with methods well-known in the technical field of formulations.

As the administration route, the most effective route is desired during the treatment, for example, oral administrations or non-oral administrations such as intravenous administration.

Administration dosages are exemplified as tablets, powders, granules, syrups, injections and the like.

As a liquid formulation suitable for oral administration, such as syrups, can be prepared from the following substances, including water, saccharide such as sucrose, sorbitol, fructose and the like; alcohols such as polyethylene glycol, polypropylene glycol and the like; oils such as sesame oil, olive oil, soybean oil and the like; preservatives such as p-hydroxybenzoic acid esters and the like; and flavoring agents such as strawberry flavor, mint and the like. In addition, tablets, powders, granules and the like can be prepared from the following substances, including excipients such as lactose, glucose, sucrose, mannitol and the like; disintegrating agents such as starch, sodium alginate and the like; lubricants such as magnesium stearate, talcum and the like; adhesives such as polyvinyl alcohol, hydroxypropyl cellulose, glutin and the like; surfactants such as fatty acid esters and the like; and plasticizers such as glycerol and the like.

Formulations suitable for non-oral administration, preferably is prepared from the sterilized aqueous agents comprising active compounds isotonic to blood of the subject. For example, under the occasion of injections, a solution for injection can be formulated from the vehicles consisting of saline, glucose solution or a mixture of saline and glucose solution.

In addition, even under conditions of non-oral agents, one or more adjuvants selected from the group consisting of diluents, preservatives, flavoring agents, excipients, disintegrating agents, lubricants, adhesives, surfactants, plasticizers and the like, as used in oral agents, can be added.

The administration amount and time of the small molecular compound of formula (I) provided in the invention depend on the age, weight, the property and severity of the symptoms to be treated. However, under general oral occasions, it is administered at an amount of 0.01 mg~1 g, preferably 0.05~50 mg per adult, once a day or several times a day. Under non-oral occasions such as intravenous administration, it is administered at an amount of 0.001~100 mg, preferably 0.01~10 mg per adult, once a day or several times a day.

The invention also relates to the use of the pharmaceutical composition provided in the invention in the preparation of stem cell drugs. The stem cell drugs refer to a class of therapeutic and/or preventive medicines for prevention and treatment of diseases resulted from loss or damage of cells by regulating proliferation and differentiation of stem cells in organisms. In recent years, it is found that traditional Chinese medicine, growth factors and small molecular compounds can regulate proliferation and differentiation of stem cells in organisms.

No specific restriction is made to stem cells as long as they are stem cells, including adult stem cells and embryonic stem cells. Adult stem cells include neural stem cells, mesenchymal stem cells, hematopoietic stem cells and the like. Embryonic stem cells as totipotent cells can be differentiated into any cell types.

The invention also relates to the use of the pharmaceutical composition provided in the invention in the preparation of medicines for treating diseases related to the loss or traumatism of cells.

In the uses according the invention, the diseases related to the loss or damage of cells include diseases related to the degeneration or damage of nervous system cells, blood system diseases, diseases related to the loss or damage of cardiovascular cells, skin diseases.

In the uses according the invention, the diseases related to the loss or damage of cells include: (1) nervous system diseases: Parkinson's disease (PD), Alzheimers disease (AD), Huntington's disease (HD), Down's syndrome, Cerebrovascular disorders, Stroke, spinal cord injury, multiple sclerosis, amyotrophic lateral sclerosis, epilepsy, anxiety disorder, depression, bipolar disorder and the like; (2) blood system diseases: acute leukemia, chronic myeloid leukemia, chronic lymphocytic leukemia, lymphoma, multiple myeloma, malignant histiocytosis, aplastic anemia, thalassemia, paroxysmal nocturnal hemoglobinuria, myelodysplastic syndrome, polycythemia vera, primary thrombocythemia, primary bone marrow fibrosis and the like; (3) cardiovascular diseases: myocardiosis, coronary heart disease, heart failure, subacute endocarditis, acute myocardial infarction, angina pectoris, ischemic heart disease and the like; (4) surgical diseases: multiple organ dysfunction syndrome, fracture nonunion, burns, bone defect, craniocerebral operation sequela, corneal injury and the like; (5) autoimmune diseases: systemic lupus erythematosus, rheumatoid arthritis, Sjogren syndrome, dermatomyositis, myasthenia gravis, multiple sclerosis, acquired immunodeficiency syndrome and the like; and diseases related to the loss or damage of other systems and cells, which are not listed here.

Any method according to the invention can be performed in vivo or in vitro.

DETAILED DESCRIPTION OF THE INVENTION

Embodiments

Figure 1:
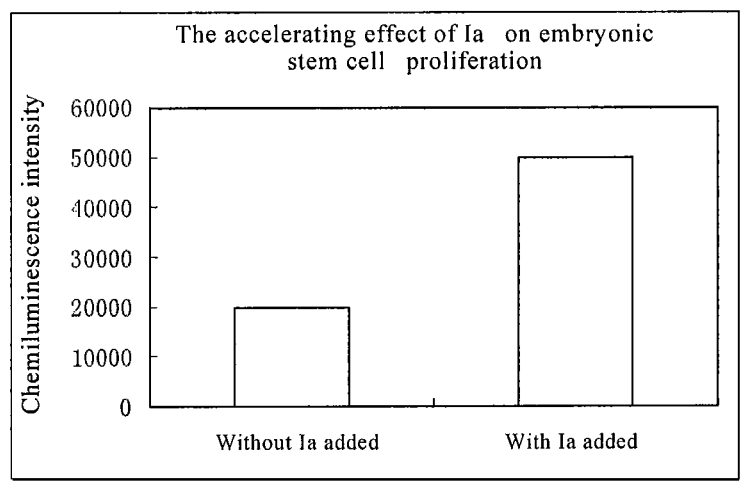
FIG. 1: the accelerating effect of Ia on embryonic stem cell proliferation

The following examples are listed to further illustrate the invention, however, the invention is not limited to the examples.

Example 1

The Preparation of 4-(4-(5-mercapto-1,3,4-oxadiazol-2-yl)phenyl) thiosemicarbazide (Ia)

Scheme I: 0.76 g (0.005M) p-Aminobenzoylhydrazide (2) is dissolved in 30 ml methanol. KOH aqueous solution (0.005M), $CS_2$ 0.3 ml (0.005M) are added, and the mixture is heated to reflux. After 24 h, methanol is removed by rotary evaporation. About 30 ml water is added, the resultant solution is acidified with 6N HCl, filtrated under vacuum, washed with ethyl ether, and dried to obtain the product 2-thiol-5-p-aminophenyl-1,3,4-oxadiazole (3); Compound 3 (579 mg) is dissolved in 20 ml methanol. KOH 168 mg and $CS_2$ 0.2 ml are added. The reaction takes place at room temperature for 4 hours. The mixture is filtrated, and methanol is removed by rotary evaporation under vacuum. Tetrahydrofuran (10 ml), toluene sulfonyl chloride (266 mg) are added. After reacting at room temperature for 1 hour, hydrazine hydrate (0.19 ml) is added. The reaction takes places at room temperature overnight. The mixture is filtrated under vacuum, recrystallized with ethanol, and dried to obtain a product (160 mg, 20% yield)

Scheme I (Synthetic route):

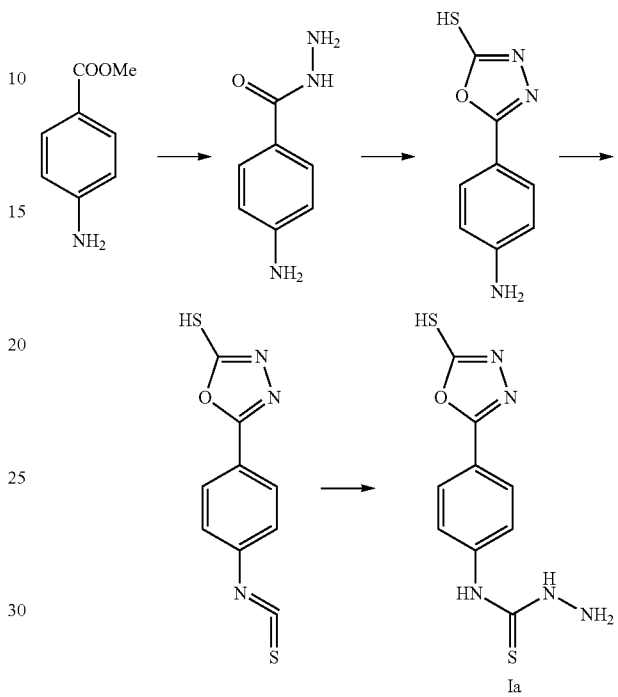

Scheme II:

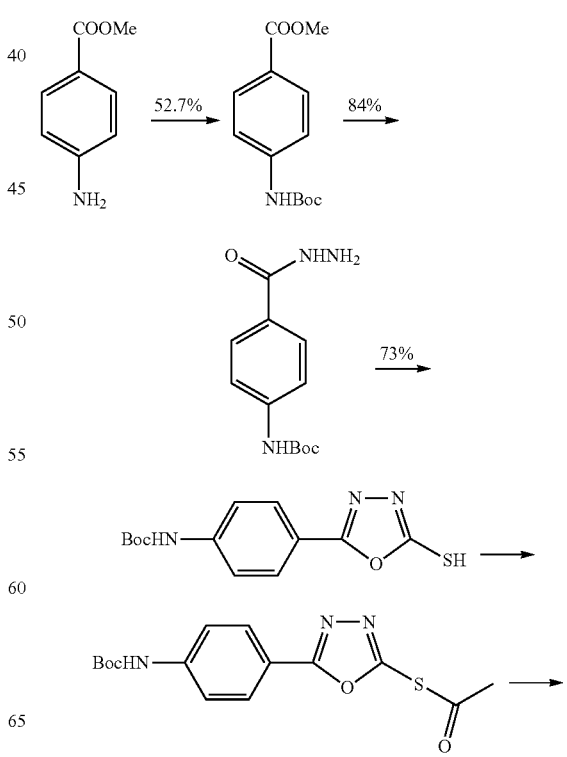

-continued

[Reaction scheme showing synthesis steps with CSCl₂, NH₂NH₂ leading to compound Ia]

IR ν (liquid paraffin) cm$^{-1}$: 3320, 3212, 1810, 1596, 1292.

1H-NMR (DMSO) δ (ppm):

2.0 (3H, s), 3.0 (1H, s), 4.0 (1H, s), 6.52 (2H, d), 7.23 (2H, d).

Example 2

Preparation of 4-(4-(5-(methylthio)-1,3,4-oxadiazol-2-yl)phenyl) thiosemicarbazide (Ib)

Compound 3 (1.5 mmol) in Example 1 and KOH (1.5 mmol) are dissolved in 11 mL anhydrous methanol. The mixture is stirred at room temperature for 10 min. CH₃I is added. The mixture is further stirred at room temperature for 4 hours. After filtration, a white solid is obtained. The white solid is washed with 5% Na₂CO₃, dried under vacuum, recrystallized with ethanol, and dried to get a product 2-methylthio-5-p-aminophenyl-1,3,4-oxadiazole (Compound 5); Compound 5 (579 mg) is dissolved in 20 ml methanol. KOH 168 mg, CS₂ 0.2 ml are added. The reaction takes place at room temperature for 4 hours. The mixture is filtrated, and methanol is removed by rotary evaporation under vacuum, Tetrahydrofuran (10 ml), toluene sulfonyl chloride (266 mg) is added. After reacting at room temperature for 1 hour, hydrazine hydrate (0.19 ml) is added. The reaction takes places at room temperature overnight. The mixture is filtrated under vacuum, recrystallized with ethanol, and dried to obtain a product (350 mg, 45% yield).

IR ν (liquid paraffin) cm$^{-1}$: 3323, 3212, 1652, 1123.

1H-NMR (DMSO) δ (ppm):

2.0 (3H, s), 2.47 (3H, s), 4.0 (1H, s), 6.52 (2H, d), 7.23 (2H, d)

Example 3

Preparation of 1-methyl-3-(4-(5-(methylthio)-1,3,4-oxadiazol-2-yl)phenyl)thiourea (Ic)

[Reaction scheme with CH₃OH, CH₃NCS]

Compound 5 (1.5 mmol) in Example 2 is dissolved in 20 mL anhydrous methanol. CH₃NCS 1.5 mmol is added. The mixture is stirred at room temperature for 5 hours. The solvent is dried by rotary exporation, recrystallized with ethanol, and dried to obtain a product Ic (350 mg, 83% yield).

IR ν (liquid paraffin) cm$^{-1}$: 3313, 3259, 1762, 1232.

1H-NMR (DMSO) δ (ppm):

2.0 (1H, s), 2.47 (6H, s), 4.0 (1H, s), 6.52 (2H, d), 7.23 (2H, d)

Example 4

The preparation of 4-(4-(5-mercapto-1,3,4-oxadiazol-2-yl)phenyl) semicarbazide (Id)

[Reaction scheme with 1. ethyl chloroformate, 2. H₂NNH₂—H₂O]

Compound 3 (965 mg) in Example 1 is dissolved in 20 ml methanol. KOH 168 mg, CS₂ 0.2 ml are added. The reaction takes place at room temperature for 4 hours. The mixture is filtrated, and methanol is removed by rotary evaporation under vacuum. Tetrahydrofuran (10 ml), ethyl chloroformate (1.08 g) are added. After reacting at room temperature for 1 hour, hydrazine hydrate (0.19 ml) is added. The reaction takes places at room temperature overnight. The mixture is filtrated under vacuum, recrystallized with ethanol, and dried to obtain a product (452 mg, 36% yield).

IR ν (liquid paraffin) cm$^{-1}$: 3320, 3212, 1632, 1292.

1H-NMR (DMSO) δ (ppm):

2.0 (2H, s), 3.0 (1H, s), 6.0 (2H, s), 7.46 (2H, d), 7.70 (2H, d)

Example 5

Preparation of (Ie)

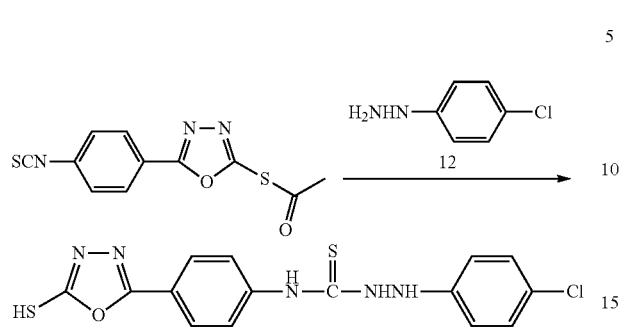

Compound 11 (10 mmol) in Scheme II of Example 1 is dissolved in methylene chloride. Compound 12 (10 mmol) is added. The mixture is heated to reflux for 6 hours. The solvent is removed by rotary exporation, the residue is recrystallized with ethanol, and dried to obtain a product Ie (3.1 g, 82% yield).

1H-NMR (DMSO) δ (ppm):
2.0 (1H), 3.0 (1H), 4.0 (2H), active hydrogen; 6.5 (4H, d), 7.2 (4H, d)

Example 6

Preparation of (If)

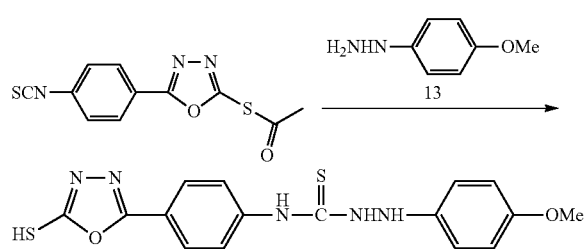

Compound 11 (10 mmol) in Scheme II of Example 1 is dissolved in methylene chloride. Compound 13 (10 mmol) is added. The mixture is heated to reflux for 12 hours. The solvent is removed by rotary exporation, the residue is recrystallized with ethanol, and dried to obtain a product If (2.6 g, 70% yield).

1H-NMR (DMSO) δ (ppm):
2.0 (1H), 3.0 (1H), 3.8 (3H, s) 4.0 (2H), active hydrogen; 6.5 (4H, d), 6.7 (2H, d), 7.2 (2H, d)

Example 7

Preparation of 1-methyl-3-(4-(5-oxo-4,5-dihydro-1,3,4-oxadiazol-2-yl)phenyl)thiourea (Ig)

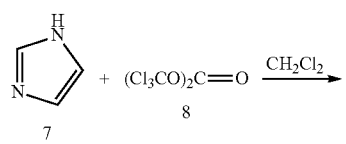

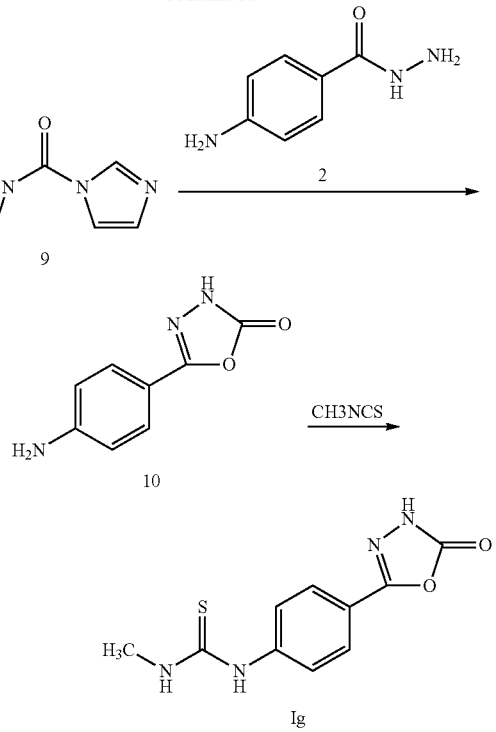

Imidazole (10 mmol) is dissolved in methylene chloride. Compound 8 (10 mmol) is added. The reaction takes place in ice bath for 1 hour and at room temperature for 2 hours. After rotary exporation of solvent, DMF (30 ml), compound 2 (10 mmol) are added. After reacting at room temperature for 24 hours, $CH_3NCS$ (10 mmol) is added. The mixture is stirred at room temperature for 5 hours. The solvent is removed by rotary exporation, the residue is recrystallized with ethanol, and dried to obtain a product Ig (1.4 g, 57% yield).

IR ν (liquid paraffin) $cm^{-1}$: 3115, 1821, 1662, 1189.

1H-NMR (DMSO) δ (ppm):
2.0 (1H, s), 2.47 (3H, s), 4.0 (1H, s), 6.5 (2H, d), 7.0 (1H, s), 7.4 (2H, d)

Example 8

Studies on the Effect of Small Molecular Compound Ia on Embryonic Stem Cell Proliferation Embryonic stem cell (obtained from oosperm according to the conventional method) is cultured in serum free medium (a conventional medium, such as DMEM/F12, αMEM, 1640, etc.). The experiments are divided into control group, FGF group, neural stem cells proliferation accelerator Ia group, FGF+neural stem cells proliferation accelerator Ia group. After culturing for 1 to 4 days, the kit CellTiter-Glo®Luminescent Cell Viability Assay (Promega) is used to detect cells proliferation by ATP method. The ATP method is performed in accordance with operational steps of the kit.

As shown in FIG. 1, the height of the histogram represents chemiluminescence intensity, which is proportional to the number of cells. It can be seen that in the presence of neural stem cells proliferation accelerator Ia, embryonic stem cell proliferation is significantly increased. Therefore, Ia accelerates the proliferation of embryonic stem cells.

Example 9

Studies on Capability of Small Molecular Compound Ia to Accelerate Rat Neural Stem Cell Proliferation Rat neural stem cells are cultured in serum free medium. The experiments are divided into control group, FGF group, small molecular compound Ia group, and FGF+small molecular compound Ia group. The detection is carried out by ATP method (see the method in Example 6). Small molecular compound Ib, Ic, Id, Ie, If, Ig also conduct said experiment.

The experimental results are shown in the following table. It is found that small molecular compound Ia, Ib, Ic, Id, Ie, If, Ig accelerate rat neural stem cell proliferation

TABLE

The accelerating effect of small molecular compound (Ia-e) on rat adult neural stem cell proliferation

| small molecular compound | proliferation rate of neural stem cells in rat |
| --- | --- |
| Ia | 4.2 |
| Ib | 2 |
| Ic | 1.5 |
| Id | 1.7 |
| Ie | 2.5 |
| If | 2.3 |
| Ig | 2.4 |

Example 10

Acceleration of the Proliferation of the Cell Line that is Cultured in Vitro, i.e., Human Neural Stem Cells Human neural stem cells (provided according to conventional methods by Peking University Stem Cell Research Center) is prepared into a single cell suspension by using a medium (DMEM/$F_{12}$+10% fetal bovine serum+20 ng/mlEGF, bFGF), and is seeded at $2\times10^4$/well on 96-well plate. The experiments are divided into medium control group (a group without adding a medicine); medium+small molecular compound Ia group (a group with a medicine added). After culturing for 4 days, MTT (5 mg/ml) 10 ul is added. After incubating for 4 hours, a 100 µl lysis solution (10% SDS, 0.1% $NH_4Cl$) is added. The mixture is incubated overnight. The light absorption value is detected at 490 nm.

Figure 2:
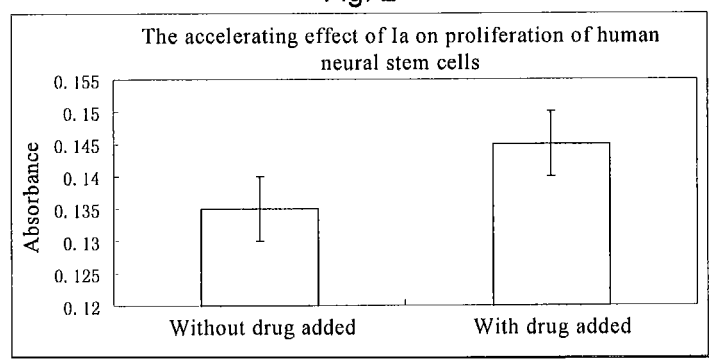
FIG. 2: the accelerating effect of Ia on proliferation of human neural stem cells

The experimental results are shown in FIG. 2, the height of the histogram represents absorbance, which is proportional to the number of cells (which has the same vertical coordinate in the MTT method, and is not explained one by one). Small molecular compound Ia has a greater absorption value, indicating that the group with small molecular compound Ia added has more cells. Therefore, it demonstrates that small molecular compound Ia accelerates human neural stem cell proliferation.

Example 11

The Accelerating Effect of Ia on Human, Rat Mesenchymal Stem Cell Proliferation

Human (rat) mesenchymal stem cells (a cell line obtained according to conventional method) is prepared into a single cell suspension by using a medium (α-MEM+10% fetal bovine serum), and is seeded at $1\times10^4$/well on 96-well plate. The experiments are divided into medium control group; and medium+small molecular compound Ia group. After culturing for 2 days, MTT (5 mg/ml) 10 ul is added. After incubating for 4 hours, a 100 µl lysis solution (10% SDS, 0.1% $NH_4Cl$) is added. The mixture is incubated overnight. The light absorption value is detected at 490 nm.

Figure 3:
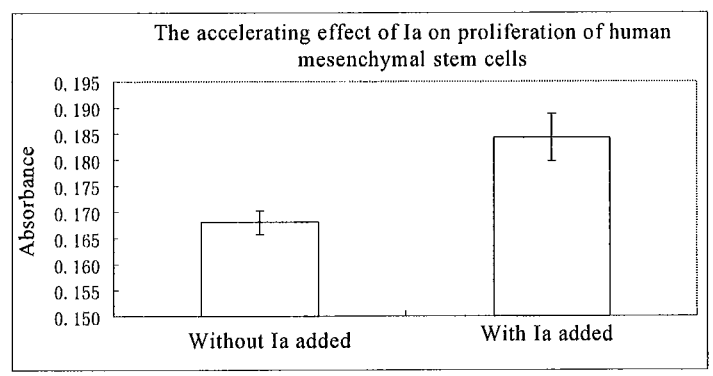
FIG. 3: the accelerating effect of Ia on proliferation of human mesenchymal stem cells
Figure 4:
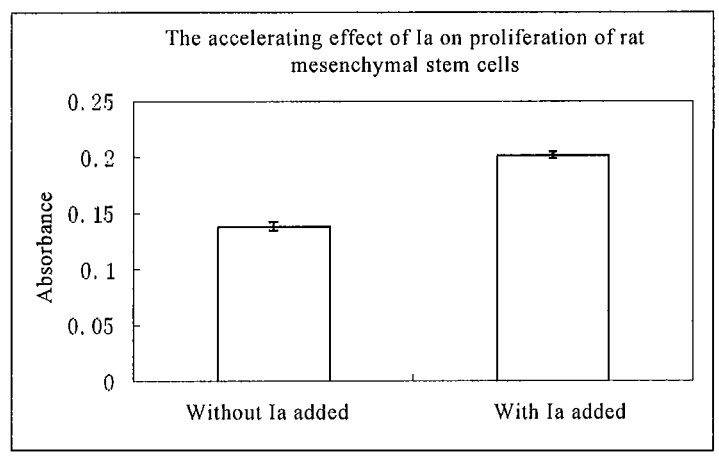
FIG. 4: the accelerating effect of Ia on proliferation of rat mesenchymal stem cells

Experimental results: as shown in FIG. 3, small molecular compound Ia accelerates human mesenchymal stem cell proliferation. As shown in FIG. 4, small molecular compound Ia accelerates rat mesenchymal stem cell proliferation.

Example 12

Formulation

Example (1)

Ia Injection

Small molecular compound Ia 9 mg is weighted, and is dissolved in 1.8 ml DMSO. After dissolution, the mixture is homogeneously stirred in physiological saline for injection (500 ml). The mixture is filtrated with sand core funnel No. 5, is subpackaged, is subjected to heat sterilization at 100° C. for 30 minutes, to leak hunting, and to quality testing, and is packaged to obtain 90 ug/5 ml/Ampoule, total for 100 Ampoules.

Example (2)

Tablets of Ia

Tablets of small molecular compound Ia are prepared by mixing the following components at said ratio by weight:

| Compound Ia | 5 | lactose | 62 |
| --- | --- | --- | --- |
| potato starch | 30 | polyvinyl alcohol | 2 |
| magnesium stearate | 1 | | |

Fine powder of compound Ia, lactose, and potato starch are mixed homogeneously. Additional polyvinyl alcohol is taken to prepare a 50% aqueous solution, which is added to the mixing powder at said mass ratio. The mixture is mixed homogeneously and is prepared into wet granules by passing screen 20 mesh, and then is subjected to fluidized drying at 60° C. Granulator is used to granulate the Ia granules obtained from said process, so as to provide Ia granules of 80-12 mesh. Magnesium stearate of greater than 60 mesh is weighted according to the ratio by weight, and is mixed with the Ia granules obtained from said process for 5 minutes, so as to ensure the homogeneity. Tablet machine is used to tablet the mixing powder of Ia, wherein the hardness reaches above 1 kg, a deviation by weight is controlled between ±5%, and the standard is 10 mg/tablet; the resultant Ia is subpackaged according to the requirement of quality and market.

Example 13

Pharmacodynamic Evaluation of Small Molecular Compound Ia in AD Rat

Establishment of AD rat model: in the experiment, stereotaxic instrument and micro-injection pump are used to inject aggregated Aβ1-40 (5 ug/ul) 2 ul (0.4 ul/min, 5 min) to the dorsal blade of the dentate gyrus in the hippocampus of rat (3.0 mm behind anterior fontanelle, open at right 2.0 mm, subdural 3.2 mm, Incisor hook plane is 2.4 mm lower than the interaural line plane), the model is established after 2 weeks.

Division of experimental groups (8-10 rats per group): physiological saline group (physiological saline is intracerebrally injected, and DMSO physiological saline is injected to tail vein); model group (Aβ1-40 is intracerebrally injected, DMSO physiological saline is injected to tail vein); a high, medium, low dose administration groups (Aβ1-40 is intracerebrally injected, and DMSO physiological saline of Ia is injected to tail vein) and positive drug (active drug 1: bFGF; positive drug 2: galantamine) control group. Administration lasts for 14 days.

Pharmacodynamic experiment (Morris water maze): the experimental apparatus is a rustless steel round pool with a height of 60 cm, and a diameter of 150 cm (both the bottom and wall of the pool are covered by black paster to facilitate the video camera for distinguishing the white rats in pool), the video camera is connected to a computer; the pool is divided into four quadrants, and a platform is placed in the middle of the first quadrant. When the experiment is carried out, the depth of water is about 40 cm, and the platform is about 2 cm below the platform, and the temperature of water is kept at 22±1° C. The experimental rats enter water from four different positions, the video camera records the swimming paths of each experimental rats, and the experimental results are analyzed by image processing software. The experiment is performed for 5 days. The day before the formal test, each rat is allowed to swim in the pool for 2 min to adapt to the environment. The first four days are the experimental phase of orientation and navigation. During the experiment, the time the rat taken from entering water to climbing onto the platform (i.e., escape latency) is recorded, and the rat is allowed to stay on the platform for 10 sec. For each experiment, rats are allowed to swim for 120 sec to find the platform. If the rats do not find the platform after 120 sec, the experimental rats are guided to the platform and stay there for 10 sec. Each rat is tested twice everyday. The rat enters water at a different position after 10 min since the first experiment finished. The platform is removed at the fifth day, and spatial exploration is carried out. The escape latency of the animals, times of rearing up, and spatial bias are recorded and compared.

Figure 5:
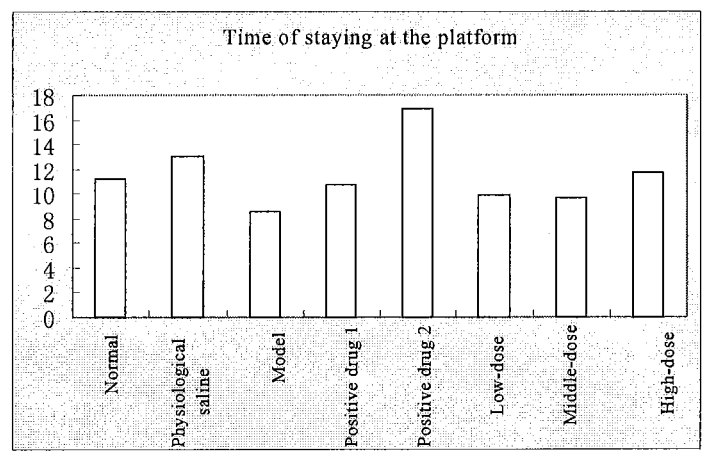
FIG. 5: pharmacodynamic evaluation (water maze result)

Test result as shown in FIG. 5: the longer the rat stays at the platform, the better ability of learning and memory it has. Both the administration group and positive drug group have improved ability of learning and memory, demonstrating small molecular compound Ia improves the symptom of AD.

Example 14

The Effect of Small Molecular Compound Ia on Neural Cells in AD Rat

The rats in Example 13 are perfused and their brains are taken. Rats are anesthetized with 10% chloral hydrate (0.3 ml/100 g). Heparin (200 ug/kg) is injected to the left ventricular, and the right atrial appendage is cut off. 40 ml physiological saline and then 300 ml 4% paraformaldehyde are perfused to the left ventricular to harden the brain. Brain taken: after breaking the neck, the skull is peeled to expose olfactory bulb, peeling it from olfactory bulb with a small curved scissor. After optic nerve is cut off, it is slowly peeled to naturally fall, the adhesion sites are cut off, and are placed into 4% paraformaldehyde solution overnight. It is dehydrated with gradient alcohol and is embedded in olefin, sectioned and floated.

HE staining: dewaxing with dimethylbenzene twice, each for 3 min. Hydration: hydration with descending concentration gradient alcohol: 100%→95%→90%→80%→70%. Dehydration lasts for 2~3 mins to remove dimethylbenzene during each gradient. Water washing: ethanol is removed. It is dipped into a hematoxylin solution for 5-10 mins, and washed with tap-water. It is dipped into a dilute hydrochloric acid-ethanol solution to carry out color separation for only a few seconds. It is washed with tap-water and dipped into dilute ammonia to make the cell nucleus blue for 3-5 mins. Then, it is washed with tap-water and dipped into Eosin solution for 5-10 mins, and washed with tap-water. After dehydration with gradient alcohol, clearing is carried out with dimethylbenzene for three times, each for 1 min. It is mounted with neutral resin, and observed by fluorescence microscopy.

It is observed by fluorescence microscopy that normal cells exhibit pink cytoplasm and blue cell nucleus.

Figure 6:
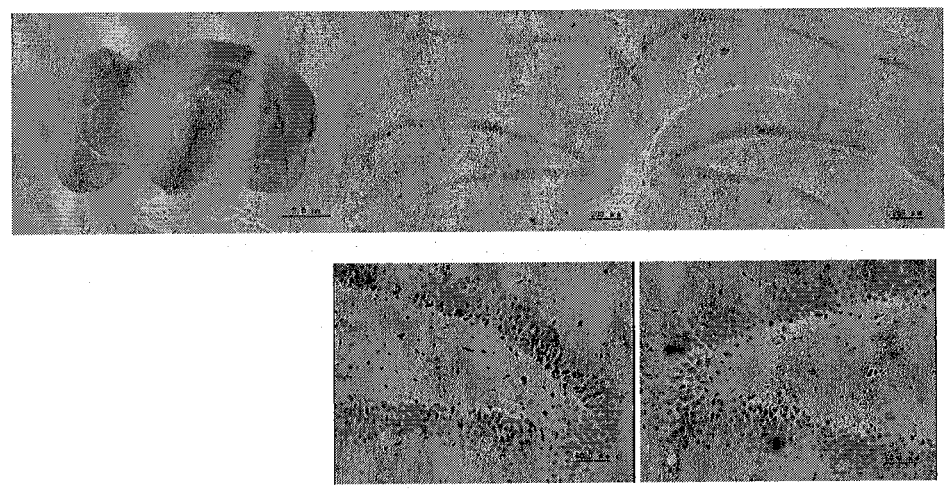
FIG. 6: the effect of Ia on the neural cells in AD rat
Figure 6:
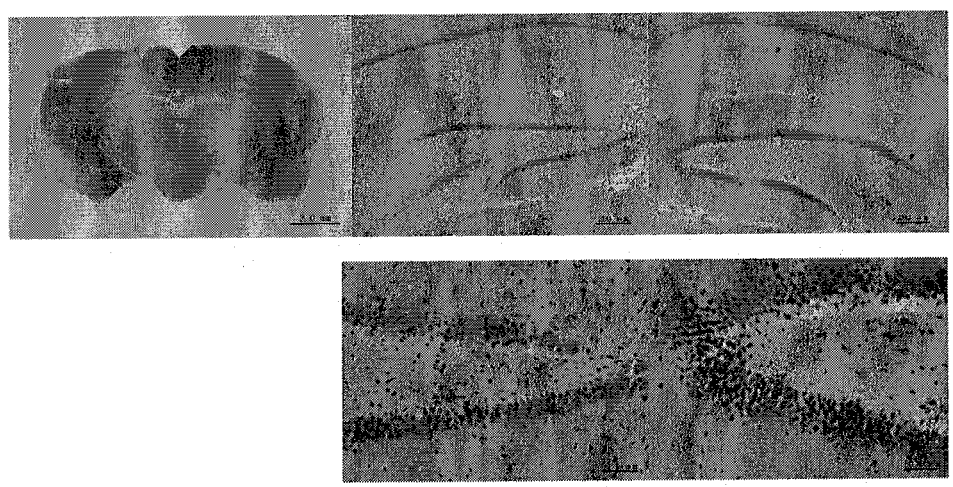
Figure 7:
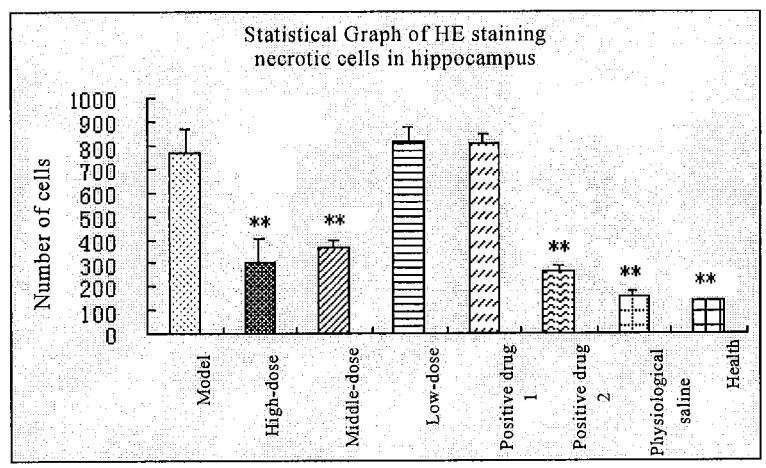
FIG. 7: Statistical Graph of HE staining of necrotic cells in hippocampus

The experimental results as shown in FIG. 6 and FIG. 7, the hippocampus cells of AD model is degenerated seriously, whereas the hippocampus cells treated with Ia is less seriously degenerated, and it is in a dosage-dependent relationship. Hence, the experiment demonstrates that Ia has an protective effect on neural cells and protects the neural cells from degeneration under exogenous stimulation.

The invention claimed is:
1. A compound selected from the group consisting of compounds (1)-(7):

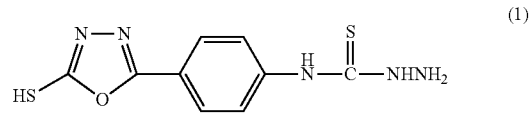

(1)

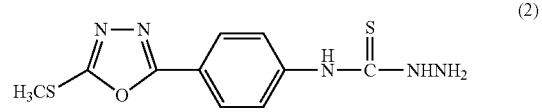

(2)

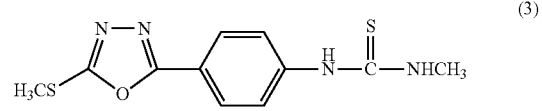

(3)

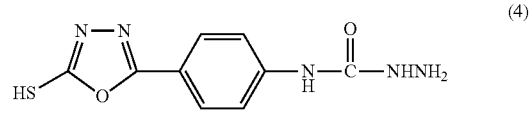

(4)

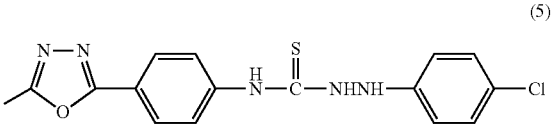

(5)

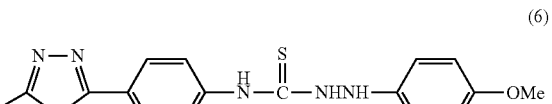

(6)

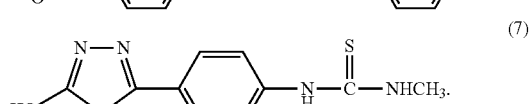

(7)

2. A method for accelerating proliferation of stem cells, comprising contacting the compound according to claim 1 with stem cells.

3. A pharmaceutical composition, comprising the compound according to claim 1 or pharmaceutically acceptable salts, or hydrates thereof.

4. A method for accelerating proliferation of stem cells in a culture medium, comprising adding the compound according to claim 1 to the medium.

\* \* \* \* \*